United States Patent [19]

Fisher

[11] Patent Number: 5,265,620
[45] Date of Patent: Nov. 30, 1993

[54] FECAL SPECIMEN SAMPLING AND TEMPERATUER MEASURING DEVICE

[76] Inventor: David W. Fisher, #1 Leisure La., Houston, Tex. 77024

[21] Appl. No.: 844,619

[22] PCT Filed: Aug. 7, 1990

[86] PCT No.: PCT/US90/04414

§ 371 Date: Mar. 27, 1992

§ 102(e) Date: Mar. 27, 1992

[51] Int. Cl.[5] ............................................ A61B 5/00
[52] U.S. Cl. ........................................ 128/736; 128/751; 128/749; 604/3; 374/141
[58] Field of Search ............... 128/736, 749, 752, 753, 128/754, 757, 758, 759, 751; 206/306, 364, 363; 374/141, 155, 157, 158; 604/1, 2, 3

[56] References Cited

U.S. PATENT DOCUMENTS

| | | | |
|---|---|---|---|
| 856,768 | 6/1907 | Comins | 374/141 |
| 2,523,691 | 9/1950 | Fitch | 374/157 |
| 2,969,141 | 1/1961 | Katzin | 374/209 |
| 3,604,420 | 9/1971 | Vaillancourt | 604/323 |
| 3,783,998 | 1/1974 | Brush et al. | 128/749 |
| 3,800,781 | 4/1974 | Zalucki | 128/749 |
| 3,822,593 | 7/1974 | Oudewaal | 73/343 |
| 3,826,259 | 7/1974 | Bailey | 604/310 |
| 4,263,921 | 4/1981 | Trugillo | 128/736 |
| 4,562,043 | 12/1985 | Mennen et al. | 422/56 |
| 4,707,450 | 11/1987 | Nason | 435/295 |
| 5,069,224 | 12/1991 | Zinnanti, Jr. | 128/752 |

Primary Examiner—Max Hindenberg
Assistant Examiner—Guy V. Tucker
Attorney, Agent, or Firm—Daniel N. Lundeen; Andrew S. Pryzant

[57] ABSTRACT

Disclosed is a combination thermometer and fecal specimen sampling device which permits the concurrent sampling of a fecal specimen and measuring of body temperature from a single penetration of the rectum. The sheath comprises an elongated, rigid, cylindrical sheath with a partially cutaway distal end to form a scoop. The thermometer is inserted into an annular bore in the sheath.

12 Claims, 2 Drawing Sheets

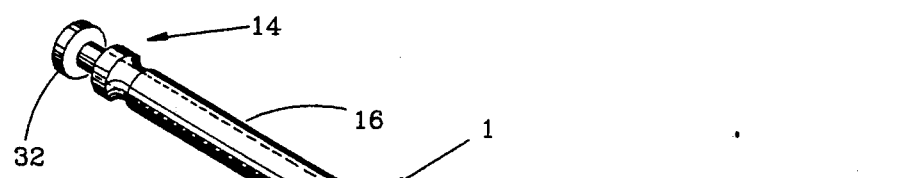
FIG. 1
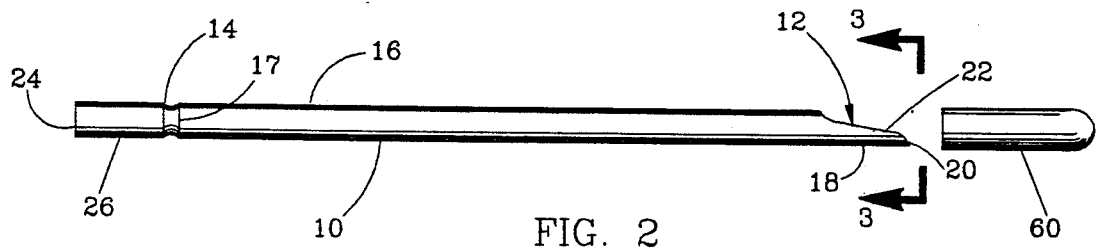
FIG. 2
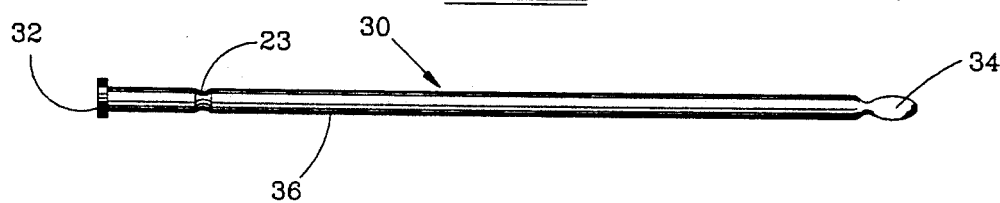
FIG. 4
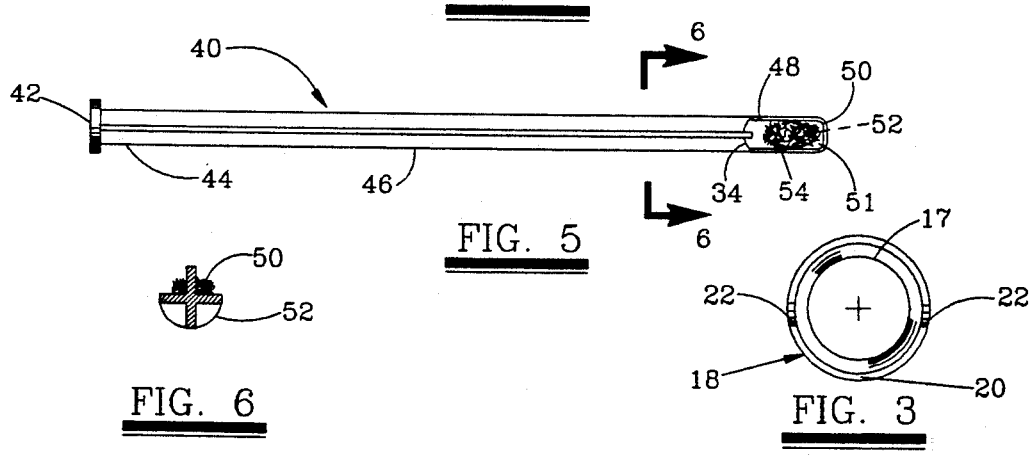
FIG. 5
FIG. 6
FIG. 3

FECAL SPECIMEN SAMPLING AND TEMPERATUER MEASURING DEVICE

FIELD OF THE INVENTION

This invention relates to a fecal specimen sampling device and more particularly to a fecal specimen sampling device having analyzing and temperature measuring elements.

BACKGROUND OF THE INVENTION

There are a number of specimen-taking devices known in the prior art. Similarly, there are a variety of thermometers known in the prior art. Heretofore, these devices have been independent of one another.

There are some sheathed thermometers taught in the prior art. One such sheathed thermometer is taught in U.S. Pat. No. 3,190,436 to Diamant. Diamant teaches a typical clinical thermometer having a tubular glass shell. The thermometer is encased in a tubular sheath of near transparent elastomeric plastic at its bulb end. The sheath includes a tab at its upper end which allows for the removal of the sheath after the thermometer has been used to measure bodily temperature.

U.S. Pat. No. 2,969,141 to Katzin teaches a thermometer cover formed of a thin, elastic material. The sheath is closed at one end and open at the other allowing the bulb end of the thermometer to be inserted into the sheath such that it residues in the closed end. The thermometer has been used to take a measurement without physical contact between the thermometer and the body on either side of the sheath.

U.S. Pat. No. 738,960 to Vaughan teaches what is described as a clinical thermometer shield. The shield is actually a thin hollow sheath which is rolled onto and off of the thermometer. It can basically be described as a prophylactic for a thermometer.

U.S. Pat. No. 4,351,616 to Farnstrom et al. teaches an antiseptic guard for a clinical thermometer. The device includes a sheath which includes a flat bendable flap at that point of the sheath extending below the bulb of the thermometer such that the flap will bend over to provide a smooth surface when the thermometer is being inserted in a bodily orifice.

U.S. Pat. No. 4,297,944 to Catlin teaches a disposable sheath for use with clinical measurement probes such as thermometers. Catlin actually utilizes both an inner and an outer sheath which are connected to each other at their distal ends and wherein the outer sheath overlies the inner sheath while the probe is in use. After the probe is withdrawn, the outer sheath is pulled longitudinally such that it inverts thereby leaving no portion of the sheath which was inserted into a bodily orifice exposed.

U.S. Pat. No. 3,800,781 to Zalucki teaches a specimen-taking device in which the gathering member and stem reside in an insertion tube by means of a diaphragm. The Zalucki device includes an enclosed end cap.

U.S. Pat. No. 3,783,998 to Brush et al. teaches a sampling syringe for collection of fecal samples. This syringe comprises a syringe barrel into which a sample may be drawn by aspiration through the use of a plunger slidable within the syringe barrel.

U.S. Pat. No. 3,650,153 to Schwab teaches yet another sleeve for use with thermometers.

The Applicant has no knowledge in the prior art of a combination fecal specimen sampling and temperature measuring device comprising a cylindrical sheath having a bore and a partially cut away distal end wherein the distal end forms a scoop and the thermometer is inserted into the bore.

SUMMARY OF THE INVENTION

A combination thermometer and fecal specimen sampling device permits the concurrent sampling of a fecal specimen and the measuring of body temperature from a single penetration of the rectum. Furthermore, a fecal specimen analyzing means is provided for performing a quick and simple on-the-spot analysis of the fecal specimen, or preserving means for maintaining the fecal specimen integrity for later laboratory work.

In one embodiment the present invention comprises a fecal specimen sampling and temperature measuring device in combination suitable for insertion into the rectum comprising a sheath having an interior bore throughout open proximal and distal ends. The distal end is longitudinally partially cut away to form a scoop whereby the fecal specimen is collected and contained. A thermometer is internally inserted into the bore and removably secured. In a preferred slide inhibiting means, the diameter of the bore has similar dimensions to the diameter of the thermometer. A cap enclosing the exterior surface of the sheath may also be included.

In another embodiment, the present invention comprises a plunger containing an analyzing means utilized to contact the fecal specimen with an analyzing fluid. The analyzing means preferably comprises a blanket containing a test fluid in a frangible ampoule.

BRIEF DESCRIPTION OF THE DRAWINGS

FIG. 1 is an isometric view of the sheath and thermometer of the present invention.

FIG. 2 is a side elevation view of the sheath and cap of the present invention.

FIG. 3 is a cross-sectional view of the sheath of the present invention taken along the lines 3—3 of FIG. 2.

FIG. 4 is a side elevation view of a thermometer in an embodiment of the present invention.

FIG. 5 is a side elevation of the plunger in an embodiment of the present invention.

FIG. 6 is a cross-sectional view taken along lines 6—6 of FIG. 5.

DESCRIPTION OF THE PREFERRED EMBODIMENT

Figure 7:
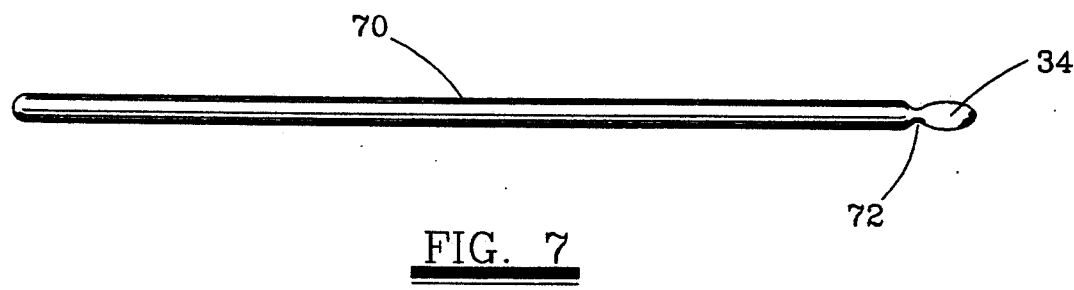
FIG. 7 is a side elevation view of a thermometer in an embodiment of the present invention.

Referring to FIG. 1, there is shown a fecal specimen sampling sheath 10 of the present invention and a combined fecal specimen sampling and thermometer measuring device 1.

The sheath 10, as seen in FIG. 2 has an interior bore 24 and exterior surface 16 with a diameter suitable for insertion into the rectum. The sheath 10 preferably comprises a cylindrical, elongated and substantially rigid tube. The bore 24 includes a thermometer 30 or a plunger 40 inserted therein. The sheath 10 is designed so that the interiorly inserted thermometer 30 is removably secured and inhibited from sliding in the sheath 10 yet may be easily inserted before use and withdrawn after use, but the plunger 40 can easily slide therein.

Figure 8:
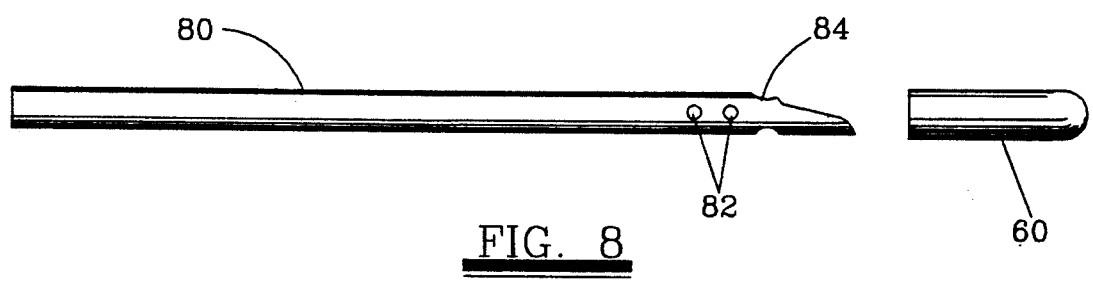
FIG. 8 is a side elevation view of an alternate sheath of the present invention having at a distal end inwardly radially extending shoulder and vent holes.
Figure 10:
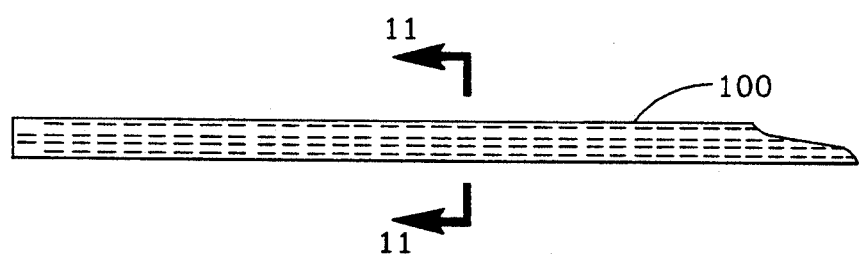
FIG. 10 is a side elevation view of the sheath of FIG. 9 having longitudinal fins along the walls of the bore.
Figure 11:
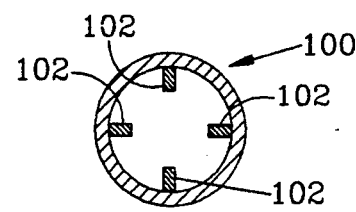
FIG. 11 is a cross-sectional view of the sheath of FIG. 10 along the lines 11—11.

The sheath 10 has a proximal end 14 and distal end 12. In one embodiment, (FIG. 2), at the proximal end 14 is a radially inwardly extending shoulder 15 narrowing the diameter of the bore 24. Corresponding to the shoulder 15 is an annular groove 23 radially inwardly cut into the thermometer 30. The shoulder 15 and the groove 23 provide one preferred means for inhibiting sliding of a thermometer 30 in the sheath 10. In another embodiment, (FIG. 9), a sheath 90 has no shoulder 15 and the preferred slide inhibiting means is provided by the bore 24 having a diameter closely dimensioned to a diameter of the thermometer 30 or 70. In a preferred embodiment, the bore 24 is slightly out of round, or of oval transverse cross-section to removably secure a thermometer inserted therein, wherein the thermometer 30 is, for example, triangularly transversely cross-sectionally shaped to tightly engage at the small-diameter surfaces of the bore 24, or release therefrom for removal of the thermometer 30 from the bore 24 by suitable rotation of the thermometer 30. In a further embodiment, as seen in FIG. 8, a sheath 80 is provided a radially, inwardly extending distal end shoulder 84 suitable for receiving a groove 72 on the thermometer 70 thereby inhibiting free sliding of the thermometer 70 in the sheath 80. In yet a further embodiment, as seen in FIGS. 10-11, a sheath 100 is provided with a plurality of radially distributed longitudinal fins 102 projecting inwardly into the interior walls of bore 24. The fins 102 engage the thermometer outside surface to removably secure the thermometer inserted therein. The fins 102 have, for example, dimensions of about 0.25 mm width and about 0.38 mm length. Other removably securing means known in the art may also be suitable.

At an open distal end 12 of sheath 10, the exterior surfaces 16 is longitudinally partially cut away to form a scoop 20, preferably comprising an arc of 180° or more as seen in FIGS. 1, 2 and 3. The scoop 20 has preferably rounded side 22 to smooth out rough edges and sharp points so that sheath 10 of device 1 presents no contusion or laceration hazard when inserted into the rectum.

The sheaths 10, 80 or 90 may include one or more vent holes 82 to allow air to escape from the sheath when a cap 60 is used to cover the sheath and the plunger 40 is inserted therein.

The sheath 10 may be manufactured from a thermoplastic material exemplified by polyacrylics, e.g. acrylic-Br, polycarbonates, and the like; metallic material such as aluminum, stainless steel, and the like; or glass. The acrylic-Br plastic is preferred.

When device 1 is utilized to measure temperature while removing a fecal specimen, the thermometer or temperature measuring implement is inserted into the central bore 24 of sheath 10. In one embodiment, the temperature measuring implement is shown in FIG. 4. The thermometer 30 has a bulbous distal end 34 and a proximal flange end 36 wider in diameter than the bore 24. The flange 36 assists withdrawal of the thermometer 30. In another embodiment shown in FIG. 7, the thermometer 70, well known in the art as a rectal thermometer, has a bulbous distal end 34 but no flange end and bulbous end 34 defines the groove 72.

Figure 9:
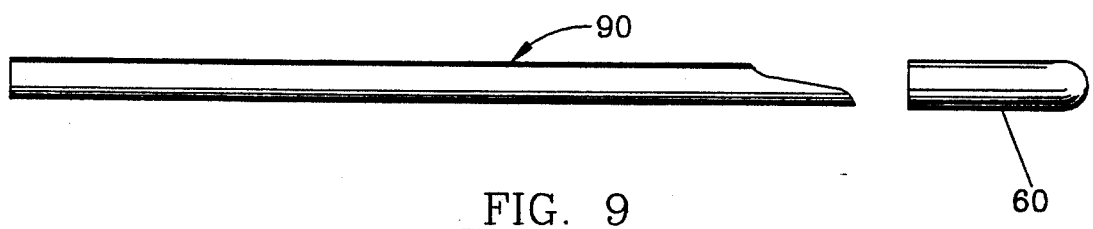
FIG. 9 is a side elevation view of the sheath of FIG. 2 absent a proximal end inwardly radially extending shoulder.

In a preferred embodiment, the present invention is manufactured from an acrylic-Br plastic extruded into the elongated, rigid tube 90 as seen in FIG. 9. For use with a CORNELL thermometer, for example, the outside diameter is nominally 6.5 mm and the bore diameter is 4.95 mm; the cut-away scoop 20 has a nominally 19 mm length and the overall sheath length is nominally 10.2 cm. These dimensions can, of course, be varied for use with other conventional thermometers. The off-the-shelf rectal thermometer 70, as seen in FIG. 7, is removably secured in the interior bore 24 so that the temperature sensing end 34 is adjacent the distal sheath end scoop 20. The overall length of the sheath is preferably shorter than the inserted thermometer 70 and the plunger 40. The length of the scoop 20 is sufficient to provide sufficient volume in the scoop end.

In another embodiment of the present invention, the interior bore 24 of the fecal specimen sampling sheath 10 has inserted therein, a cylindrical shaped plunger 40 having a fecal specimen analyzing means 52 disposed at a distal end 48. As seen in FIGS. 5 and 6, the plunger 40 also has a proximal end flange 42 wider in diameter than the bore 24. The flange 42 assists withdrawal of the plunger 40 from the sheath 10. The distal end 48 of the plunger 40 is preferably concave shaped to provide a cup 50 for holding the analyzing means 52. Analyzing means 52 is suitable for performing simple tests on the fecal specimen sample obtained by the sheath 10. The analyzing means 52 generally comprises a frangible ampoule (not shown) embedded in a blanket or gauze member 54 such as, for example, cotton or another fiber wetted by an analyzing solution contained in such frangible ampoules. Examples of such tests include an occult blood test, a Guaiac test, and the like well known in the art. When the frangible ampoule contains the Guaiac test fluid, the analyzing fluid typically comprises a weak hydrogen peroxide solution in ethanol. An ordinary practitioner in the art will be familiar with the various tests conducted on fecal specimens and appropriate reagents utilized therefor which may be contained in the frangible ampoule.

In the practice of the present invention, when a medical or veterinary practitioner desires to sample the fecal specimen of a patient, a sufficient length of the fecal specimen sampling device 1 is inserted into the patient's rectum to gently sample a fecal specimen within the distal scoop 20. The device 1 may have to be gently swiveled and/or pivoted in order to withdraw an acceptably large specimen. Upon withdrawal, the thermometer is read and removed from the sheath. The specimen which is contained within the central bore 24 may then be covered with the cap 60 to prevent outside contact with the sample contained in scoop 20 and exterior surfaces of the sheath 10 that have penetrated the rectum. The cap 60 typically has an inside diameter closely matching the outside diameter of sheath 10 whereby the cap 60 covering the sheath 10 may be held firmly. The sample may then be analyzed by analyzing means 52 and/or sent to a laboratory for analysis.

When it is desired to conduct a quick single-step test on the fecal specimen contained in the sheath 10 following use of device 1, the plunger 40 may be utilized to bring into contact the analyzing reagents contained in the cupped region 50 on plunger 40 with the fecal specimen residing in the scoop 20 of sheath 10. In this manner, the fecal specimen may be quickly analyzed without having to send the specimen off to the laboratory. The analyzing reagents in frangible ampoule are released typically by breaking the ampoule under hand pressure. Generally, the sheath 10 is covered by the cap 60 and the plunger 40 is then inserted into the bore 24 of sheath 10 until the analyzing reagents are in contact with the fecal specimen in the distal scoop 20. The cap 60 insures no loss of analyzing fluid and good contact with the specimen. The plunger 40 is withdrawn and analysis is typically indicated by color change in the blanket 54 soaked with the analyzing reagents and contacted with the fecal specimen. Both plunger and sheath may be disposed of thereafter or the capped sheath may be sent to the lab for further analysis.

When it is desired to simultaneously measure rectal temperature and take a fecal specimen, the device 1 of the present invention includes the temperature measuring implement inserted into the bore 24 of sheath 10. To obtain an accurate temperature reading, the thermometer 30, for example, should be inserted into the sheath 10 so that the temperature sensing bulbous end 34 resides in the distal scoop end 12 of sheath 10. Device 1 is then inserted into the rectum for a period of time sufficient to obtain an accurate temperature measurement. Following the sampling procedures mentioned above, the device 1 is withdrawn and temperature read by withdrawing the thermometer 30 from the sheath 10. The analyzing procedure may next be undertaken as described previously.

The foregoing description of the invention is illustrative and explanatory thereof. Various changes in the materials, apparatus, and particular parts employed will occur to those skilled in the art. It is intended that all such variations within the scope and spirit of the appended claims be embraced thereby.

What is claimed is:

1. A device for simultaneously sampling a fecal specimen and measuring rectal temperature, comprising:
   (a) a rigid and elongated disposable tubular sheath having open proximal and distal ends, said distal end having rounded edges adapted for rectal insertion and at least partially cut away longitudinally and transversely to form a longitudinally open-ended scoop for collecting and containing a fecal specimen from the rectum;
   (b) an interior bore formed throughout said sheath; and
   (c) a thermometer removably inserted in said bore with a temperature sensing end thermally exposed adjacent said scoop for concurrently measuring rectal temperature and collecting said specimen.

2. The device of claim 1, wherein a diameter of said bore has similar dimensions to a diameter of said thermometer to inhibit sliding of said thermometer in said bore.

3. The device of claim 1, further comprising:
   (a) a cap attached to said distal end of said sheath to enclose said scoop and contain a fecal specimen therein;
   (b) a plunger for insertion into said sheath, said plunger having proximal and distal ends;
   (c) a blanket contained in said distal end of said plunger for contacting said specimen in said distal end of said sheath;
   (d) a friable fluid-carrying ampoule contained within said blanket for releasing a fluid on said blanket.

4. The device of claim 3, said fluid comprising a solution of hydrogen peroxide and ethanol.

5. The device of claim 3, wherein said distal end of said plunger is substantially concave for receiving said blanket and said fluid-carrying ampoule.

6. The device of claim 1, wherein said sheath is made of plastic, metallic or glass material.

7. The device of claim 1, wherein said sheath further comprises a radially inwardly extending shoulder at said proximal end, said shoulder engageable with a groove on said thermometer to inhibit longitudinal sliding of said thermometer in said bore.

8. The device of claim 1, wherein said interior bore is out of round for engaging said thermometer.

9. The device of claim 1, wherein said sheath includes a plurality of radially distributed longitudinal fins projecting inwardly into said interior bore.

10. The device of claim 1, wherein said scoop is formed from a circular cross-sectional arc of greater than 180°.

11. A method for sampling a fecal specimen and measuring rectal temperature, comprising the steps of:
    (a) inserting into the rectum a device comprising:
       (i) a rigid and elongated disposable tubular sheath having open proximal and distal ends, said distal end having rounded edges adapted for rectal insertion and at least partially cut away longitudinally and transversely to form a longitudinally open-ended scoop for collecting and containing a fecal specimen from the rectum;
       (ii) an interior bore formed throughout said sheath; and
       (iii) a thermometer removably inserted in said bore with a temperature sensing end thermally exposed adjacent said scoop for concurrently measuring rectal temperature and collecting said specimen;
    (b) sampling said fecal specimen with said scoop in the rectum;
    (c) measuring said temperature with said rectally inserted thermometer;
    (d) withdrawing said device from the rectum.

12. The method of claim 11, further comprising the steps of:
    (e) removing said thermometer from said sheath;
    (f) enclosing the distal end of said sheath containing the fecal specimen with a cap;
    (g) inserting a plunger into the bore in said sheath adjacent said fecal specimen, said plunger having a blanket wetted by an analyzing test fluid;
    (h) wetting said fecal specimen with said fluid; and
    (i) reading said test results.

* * * * *